(12) United States Patent
Suleiman et al.

(10) Patent No.: US 9,456,978 B2
(45) Date of Patent: Oct. 4, 2016

(54) COSMETIC COMPOSITIONS CONTAINING A SILICONE-ORGANIC POLYMER HYBRID COMPOUND

(71) Applicant: L'OREAL, Paris (FR)

(72) Inventors: Aziza Suleiman, Paterson, NJ (US); Clarissa Nogueira, Hoboken, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 13/729,121

(22) Filed: Dec. 28, 2012

(65) Prior Publication Data

US 2014/0186270 A1    Jul. 3, 2014

(51) Int. Cl.
| | |
|---|---|
| *A61Q 19/00* | (2006.01) |
| *A61K 8/58* | (2006.01) |
| *A61K 8/81* | (2006.01) |
| *A61Q 5/06* | (2006.01) |
| *A61K 8/895* | (2006.01) |

(52) U.S. Cl.
CPC .............. *A61K 8/895* (2013.01); *A61K 8/8158* (2013.01); *A61K 8/8182* (2013.01); *A61Q 5/06* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 3,836,537 A | | 9/1974 | Boerwinkle et al. |
| 6,375,932 B1 * | | 4/2002 | Hiwatashi ............ A61K 8/8141 424/45 |
| 2009/0060858 A1 * | | 3/2009 | Schwarzwaelder ...... A61Q 5/06 424/70.12 |

FOREIGN PATENT DOCUMENTS

| | | |
|---|---|---|
| DE | 102004027838 A1 | 12/2005 |
| DE | 102009054516 A1 | 6/2011 |
| FR | 1400366 | 4/1965 |
| GB | 1021400 | 5/1964 |
| KR | 20100105168 A | 2/2010 |
| WO | WO 9207545 A1 * | 5/1992 |
| WO | 2005094775 A1 | 10/2005 |
| WO | 2010025311 A1 | 3/2010 |
| WO | 2011069786 A2 | 6/2011 |
| WO | WO 2011069618 A2 * | 6/2011 |

OTHER PUBLICATIONS

Google Machine translation of KR-1020090024057, obtained Jan. 2, 2014 with text selected from KIPO PDF of unexamined application.*
Google Machine translation of WO 1992007545 A1, obtained from Google Patents Jan. 2, 2014.*
Ash et al., "stearyl alcohol", Handbook of Green Chemicals, Synapse Info Resources, (2004) p. 889.*
Schweinsberg et al. WO2011/069786 A2 Google patent machine translation, downloaded Jul. 25, 2015.*
Hoessel et al., J. Cosmet. Sci., 61: 343-352 (2010).*
Wacker Chemie AG, Belsil P 1101, Wacker Silicones Technical data sheet for Belsil P 1101, Jul. 25, 2012, Version 1.4.
Wacker Chemie AG, Simply Beautiful: A Guide to Silicones for the Cosmetic Industry.
European Patent Office, P.B. 5818 Patentlaan 2, NL-2280 HV Rijswijk, International Search Report in application PCT/EP2013/077622, mailed on May 6, 2014.

* cited by examiner

*Primary Examiner* — Kortney L Klinkel
*Assistant Examiner* — Lisbeth C Robinson
(74) *Attorney, Agent, or Firm* — Maria Luisa Balasta; Runzhi Zhao

(57) ABSTRACT

The present invention is directed towards a composition comprising, in a cosmetically acceptable carrier, at least one silicone-organic polymer hybrid compound; at least one nonionic film forming polymer; at least one amphoteric film forming polymer; and a neutralizer. The present invention also relates to methods for imparting shape to or maintaining the shape of hair wherein the composition provides style memory, strong hold and good shine, while at the same time, providing smoothness and a natural feel to the hair.

15 Claims, No Drawings

COSMETIC COMPOSITIONS CONTAINING A SILICONE-ORGANIC POLYMER HYBRID COMPOUND

FIELD OF THE INVENTION

The present invention relates to compositions for application onto keratinous substrates such as hair and skin. In particular, the present invention relates to compositions containing a silicone-organic polymer hybrid compound and film forming polymers and to methods of caring for or imparting shape to or maintaining the shape of keratinous substrates contacted with said compositions.

BACKGROUND OF THE INVENTION

Consumers of cosmetic products actively seek out multi-functional, new products which are pleasing to the senses, both on application and in use, and which have innovative, interesting and/or pleasing textures, preferably without any sacrifice to functional performance. For example, for hair care and hair treatment products, one important functional element of such compositions is their ability to condition and style the hair without weighing it down. Many consumers seek hair care products which provide a light feel, are easy to apply, moisturize, and add shine to the hair. The resulting feel and texture of the product during the application process, in addition to the feel of the hair after the application are also important elements of such commodities.

Moreover, under high humidity conditions, hair tends to absorb moisture causing it to be less manageable, which makes it more difficult to shape and style hair. Frizzy hair is particularly prone to problems when exposed to higher humidity. Applying a coating, such as a moisture barrier or a film on the hair is known to help to keep moisture out of the hair allowing for more efficient hair shaping and maintenance of hair shape, even in extreme humidity conditions. In the area of skin care, applying a film or coating on skin which can help keep the skin moisturized and/or protect the skin from extreme weather conditions is highly desirable.

Traditional compositions on the cosmetic market appear in various forms. They can range anywhere from solutions, foams, gels, creams, waxes, mousses, sprays, serums, to aerosols and can impart a variety of levels of care and cosmeticity depending on the state of the hair and skin. However, these conventional cosmetic compositions contain emulsifying systems which may have limitations and may be less appealing to the consumer. For example, the use of silicone compounds in some of these compositions to achieve desirable shine or certain textures and feel may result in other limitations. Such limitations may include sticky or greasy products, irritation on the skin/scalp, a heavy or oily feel to the hair and skin, and the use of high levels of raw materials or additional ingredients to correct for the detrimental effects of other ingredients, leading to a costly product. Therefore, there is still a need to improve currently marketed commodities in order to provide the consumer with innovative formulations that present sensory, functionality and cost-effective perspectives on cosmetic products.

The formulation of hair spray compositions, especially aerosols, is another area where formulation challenges exist. Typically, such products contain at least one volatile organic compound (VOC) in order to impart certain attributes to the hair such as good styling hold. For essentially ecological reasons and governmental regulations in various countries, it is sought or even necessary to reduce the amount of volatile organic compounds (VOCs) present in the composition. To reduce the amount of VOC and to obtain a low-VOC aerosol device, the organic solvents, for instance ethanol and dimethyl ether, are partially replaced with water, and concomitantly, with other compounds such as silicone polymers and film forming polymers, which could pose more formulation challenges. In addition, even at very low to zero VOCs, problems related with moisture sensitivity of fully water-based products have been found to be problematic from the standpoints of moisture sensitivity and eco-toxicity depending on the polymer and regional regulations.

Thus, the ability to shape and/or maintain the shape of hair, and achieve a strong styling hold, good texture and good shine on hair, while providing a clean, natural and light-weight feel to the hair remain as additional areas for improvement, particularly in connection with certain type of polymers such as silicone-based polymers.

It is thus an object of the present invention to provide a cosmetic composition for use on keratinous substrates, such as skin and hair, which provides good texture and a clean, natural and light-weight feel on the substrates. When the keratinous substrate is hair, it is also an object of the present invention to provide a composition which can impart shape and/or maintain the shape of hair, provide a strong styling hold and good shine to the hair.

SUMMARY OF THE INVENTION

The present disclosure is directed to a composition comprising, in cosmetically acceptable carrier:
(a) at least one silicone-organic polymer hybrid compound;
(b) at least one nonionic film forming polymer;
(c) at least one amphoteric film forming polymer; and
(d) at least one neutralizer.

The present invention further relates to a method of imparting cosmetic benefits to keratinous substrates.

In certain embodiments, the present invention further relates to a method of imparting shape to hair or maintaining the shape of hair comprising applying the above-described composition to the hair.

It has been surprisingly and unexpectedly discovered that the application of the above-described compositions onto keratinous substrates, such as hair and skin, resulted in desirable and beneficial effects on the substrates, for example, excellent styling effects on hair, the ability to maintain the shape of hair, manageability of hair, good texture and a desirable shine/healthy look to hair. Additional advantages can be achieved with the use of the above-described composition on keratinous substrates such as smoothness, softness, and clean/natural and light-weight/non-greasy or non-oily feel. Furthermore, the compositions of the present disclosure can impart transfer/water resistant and humidity resistant properties to keratinous substrates.

The compositions of the present invention can be formulated as a spray product having a low content of volatile organic compounds.

DETAILED DESCRIPTION

The term "comprising" (and its grammatical variations) as used herein is used in the inclusive sense of "having" or "including" and not in the exclusive sense of "consisting only of". The terms "a" and "the" as used herein are understood to encompass the plural as well as the singular.

Other than in the operating examples, or where otherwise indicated, all numbers expressing quantities of ingredients and/or reaction conditions are to be understood as being modified in all instances by the term "about," meaning within 10% to 15% of the indicated number.

"Film former" or "film forming agent" or "film forming polymer" as used herein means a polymer or resin or material that leaves a film on the substrate to which it is applied, for example, after a solvent accompanying the film former has evaporated, dried, absorbed into and/or dissipated on the substrate.

"At least one" as used herein means one or more and thus includes individual components as well as mixtures/combinations.

"Substituted," as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

Silicone-Organic Polymer Hybrid Compound

The at least one silicone-organic polymer hybrid compound of the present disclosure includes, but is not limited to, a silicone polyvinyl acetate compound.

The silicone-organic polymer hybrid compound of the present disclosure may also be chosen from a cross-linked anionic copolymer comprised of organic polymer blocks and silicone blocks, resulting in a multiblock polymer structure.

In particular, the silicone-organic polymer hybrid compound of the present disclosure may be chosen from crosslinked anionic copolymers comprising at least one crosslinked polysiloxane structural unit. Examples of these polymers have been described in the PCT publication, WO2011069786, published Jun. 16, 2011.

A particularly preferred silicone-organic polymer hybrid compound of the present disclosure is a compound having the INCI name of Crotonic Acid/Vinyl C8-12 Isoalkyl Esters/VA/Bis-Vinyldimethicone Crosspolymer which is a copolymer of Crotonic Acid, vinyl C8-12 isoalkyl esters and Vinyl Acetate crosslinked with bis-vinyldimethicone. This compound is commercially available from the company Wacker Chemie AG under the tradename Wacker Belsil® P1101 (may also be known under the tradename Wacker Belsil® P101). Crotonic Acid/Vinyl C8-12 Isoalkyl Esters/VA/Bis-Vinyldimethicone Crosspolymer is also known by the technical name of Crotonic Acid/Vinyl C8-12 Isoalkyl Esters/VA/divinyldimethicone Crosspolymer.

The at least one silicone-organic polymer hybrid compound is present in the composition of the present disclosure in an amount of from about 0.05 to about 20% by weight, such as from about 0.1 to about 10% by weight, or such as from about 0.5 to about 6% by weight, or such as from about 1 to about 3% by weight, including all ranges and subranges there-between, based on the total weight of the composition.

Nonionic Film Forming Polymer

The non-ionic fixing polymers which can be used according to the present disclosure are chosen, for example, from: vinylpyrrolidone homopolymers; copolymers of vinylpyrrolidone and of vinyl acetate; polyalkyloxazolines, such as the polyethyloxazolines provided by the company Polymer Chemistry Innovations under the names Aquazol® HP, and Aquzol® HVIS; vinyl acetate homopolymers, such as the product provided under the name UCAR™ 130 Latex Resin by the company Dow Chemical or the product provided under the name Ultrapure Polymer 2041-R 012 by the company Ultra Chemical, Inc.; copolymers of vinyl acetate and of acrylic ester, such as the product provided under the name Rhodopas AD 310 from Rhone-Poulenc; copolymers of vinyl acetate and of ethylene, such as the product provided under the name Dermacryl® LOR by the company Akzo Nobel; copolymers of vinyl acetate and of maleic ester, for example of dibutyl maleate, such as the product provided under the name Appretan MB Extra by the company Clariant; copolymers of polyethylene and of maleic anhydride; alkyl acrylate homopolymers and alkyl methacrylate homopolymers, such as the product provided under the name Micropearl RQ 750 by the company Matsumoto or the product provided under the name Luhydran® A 848 S by the company BASF; acrylic ester copolymers, such as, for example, copolymers of alkyl acrylates and of alkyl methacrylates, such as the product provided by the company Dow Chemical under the name Primal™ AC-261 K and the product provided by Evonik under the name Eudragit® NE 30 D, by the company BASF under the names Acronal® 601, Luhydran® R 8833 or 8845, or by the company Clariant under the names Appretan® N 9213 or N9212; copolymers of acrylonitrile and of a non-ionic monomer chosen, for example, from butadiene and alkyl (meth)acrylates; mention may be made of the products provided under the names Nipol LX 531 B by the company Nippon Zeon or those provided under the name CJ 0601 B by the company Rohm and Haas; polyurethanes, such as the products provided under the names Acrysol™ RM 1020 or Acrysol™ RM 2020 by the company Dow Chemical or the products Uraflex XP 401 UZ or Uraflex XP 402 UZ by the company DSM Resins; copolymers of alkyl acrylate and of urethane, such as the product 8538-33 by the company National Starch; polyamides, such as the product Estapor LO 11 provided by the company Rhone-Poulenc; and chemically modified or unmodified non-ionic guar gums.

The unmodified non-ionic guar gums are, for example, the products sold under the name Vidogum GH by the company Unipectine and under the name Jaguar® S by the company Rhodia. The modified non-ionic guar gums, which can be used according to the invention, are preferably modified by C1-C6 hydroxyalkyl groups. Mention may be made, by way of example, of the hydroxymethyl, hydroxyethyl, hydroxypropyl, and hydroxybutyl groups. These guar gums are well known in the state of the art and can, for example, be prepared by reacting the corresponding alkene oxides, such as, for example, propylene oxides, with guar gum, so as to obtain a guar gum modified by hydroxypropyl groups.

Other nonionic film forming polymers may be chosen from non-ionic guar gums optionally modified by hydroxyalkyl groups are, for example, sold under the trade names Jaguar® HP8, Jaguar® HP60, Jaguar® HP120, and Jaguar® HP 105 by the company Rhodia or under the name Galactasol™ 4H4FD2 by the company Ashland Specialty Ingredients.

The alkyl radicals of the non-ionic fixing polymers have from 1 to 6 carbon atoms, unless otherwise mentioned.

Other suitable examples of film forming polymers are fixing polymers of grafted silicone type comprising a polysiloxane portion and a portion composed of a non-silicone organic chain, one of the two portions constituting the main chain of the polymer and the other being grafted onto the said main chain. These polymers can be non-ionic.

Preferred nonionic film forming polymers of the present disclosure are chosen from vinylpyrrolidone homopolymers and copolymers of vinylpyrrolidone and of vinyl acetate. Vinylpyrrolidone homopolymers (INCI name: polyvinylpyrrolidone) are commercially available from Ashland Specialty Ingredients under the tradename PVP K. Copolymers of vinylpyrrolidone and of vinyl acetate (INCI name: VP/VA copolymer) are commercially available from BASF under the tradename Luviskol® VA.

The at least one nonionic film forming polymer is present in the composition of the present disclosure in an amount of from about 0.05 to about 15% by weight, such as from about 0.1 to about 10% by weight, and from about 0.5 to about 5% by weight, including all ranges and subranges there-between, based on the total weight of the composition.

Amphoteric Film Forming Polymer

The amphoteric film-forming polymers which can be used in accordance with the invention can be chosen from polymers containing units B and C distributed randomly in the polymer chain, in which B denotes a unit derived from a monomer containing at least one basic nitrogen atom and C denotes a unit derived from an acid monomer containing one or more carboxylic or sulphonic groups, or alternatively B and C can denote groups derived from carboxybetaine or sulphobetaine zwitterionic monomers;

B and C can also denote a cationic polymer chain containing primary, secondary, tertiary or quaternary amine groups, in which at least one of the amine groups bears a carboxylic or sulphonic group connected via a hydrocarbon radical or alternatively B and C form part of a chain of a polymer containing an α,β-dicarboxylic ethylene unit in which one of the carboxylic groups has been made to react with a polyamine containing one or more primary or secondary amine groups.

The amphoteric film-forming polymers corresponding to the definition given above which are more particularly preferred are chosen from the following polymers:

(1) polymers resulting from the copolymerization of a monomer derived from a vinyl compound bearing a carboxylic group such as, more particularly, acrylic acid, methacrylic acid, maleic acid, α-chloroacrylic acid, and a basic monomer derived from a substituted vinyl compound containing at least one basic atom, such as, more particularly, dialkylaminoalkyl methacrylates and acrylates, dialkylaminoalkylmethacrylamides and -acrylamides. Such compounds are described in U.S. Pat. No. 3,836,537.

(2) polymers containing units derived from:
a) at least one monomer chosen from acrylamides and methacrylamides substituted on the nitrogen with an alkyl radical,
b) at least one acidic comonomer containing one or more reactive carboxylic groups, and
c) at least one basic comonomer such as esters containing primary, secondary, tertiary and quaternary amine substituents of acrylic and methacrylic acids and the product of quaternization of dimethylaminoethyl methacrylate with dimethyl or diethyl sulphate.

The N-substituted acrylamides or methacrylamides which are more particularly preferred according to the invention are groups in which the alkyl radicals contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are chosen more particularly from acrylic acid, methacrylic acid, crotonic acid, itaconic acid, maleic acid and fumaric acid and alkyl monoesters, having 1 to 4 carbon atoms, of maleic or fumaric acids or anhydrides.

The preferred basic comonomers are aminoethyl, butylaminoethyl, N,N'-dimethylaminoethyl and N-tert-butylaminoethyl methacrylates.

The copolymers whose CTFA (4th edition, 1991) name is octylacrylamide/acrylates/butylaminoethyl methacrylate copolymer such as the products sold under the name Amphomer® or Balance 47 (formerly Lovocryl 47) by the company Akzo Nobel are particularly used.

(3) crosslinked and alkylated polyamino amides partially or totally derived polyamino amides.

(4) polymers containing zwitterionic units of formula:

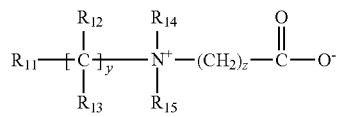

in which $R_{11}$ denotes a polymerizable unsaturated group, such as an acrylate, methacrylate, acrylamide or methacrylamide group, y and z represent an integer from 1 to 3, $R_{12}$ and $R_{13}$ represent a hydrogen atom or methyl, ethyl or propyl, and $R_{14}$ and $R_{15}$ represent a hydrogen atom or an alkyl radical such that the sum of the carbon atoms in $R_{14}$ and $R_{15}$ does not exceed 10.

The polymers comprising such units can also contain units derived from non-zwitterionic monomers such as dimethyl or diethylaminoethyl acrylate or methacrylate or alkyl acrylates or methacrylates, acrylamides or methacrylamides or vinyl acetate:

By way of example, mention may be made of the copolymer of methyl methacrylate/dimethyl carboxymethylammonio methyl ethylmethacrylate.

(5) polymers derived from chitosan.

(6) Polymers derived from the N-carboxyalkylation of chitosan, such as N-carboxymethylchitosan or N-carboxybutylchitosan sold under the name "Evalsan" by the company Jan Dekker.

(7) Polymers corresponding to the general formula below are described, for example, in French patent 1,400,366:

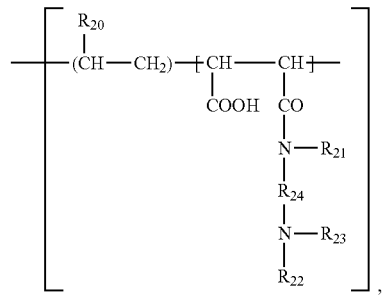

in which $R_{20}$ represents a hydrogen atom, a $CH_3O$, $CH_3CH_2O$ or phenyl radical, $R_{21}$ denotes hydrogen or a lower alkyl radical such as methyl or ethyl, $R_{22}$ denotes hydrogen or a lower alkyl radical such as methyl or ethyl, $R_{23}$ denotes a lower alkyl radical such as methyl or ethyl or a radical corresponding to the formula: $—R_{24}—N(R_{22})_2$, $R_{24}$ representing a $—CH_2—CH_2—$, $—CH_2—CH_2—CH_2—$ or $—CH_2—CH(CH_3)—$ group, $R_{22}$ having the meanings mentioned above, as well as the higher homologues of these radicals and containing up to 6 carbon atoms.

(8) Amphoteric polymers of the type -D-X-D-X chosen from:
a) polymers obtained by the action of chloroacetic acid or sodium chloroacetate on compounds containing at least one unit of formula:

$$-D-X-D-X-D- \qquad (I)$$

where D denotes a radical

and X denotes the symbol E or E', E or E', which may be identical or different, denotes a divalent radical which is an alkylene radical containing a straight or branched chain containing up to 7 carbon atoms in the main chain, which is unsubstituted or substituted with hydroxyl groups and which can contain, in addition to the oxygen, nitrogen and sulphur atoms, 1 to 3 aromatic and/or heterocyclic rings; the oxygen, nitrogen and sulphur atoms being present in the form of ether, thioether, sulphoxide, sulphone, sulphonium, alkylamine or alkenylamine groups, hydroxyl, benzylamine, amine oxide, quaternary ammonium, amide, imide, alcohol, ester and/or urethane groups.

b) Polymers of formula:

-D-X-D-X-  (I')

in which D denotes a radical

and X denotes the symbol E or E' and at least once E'; E having the meaning given above and E' is a divalent radical which is an alkylene radical with a straight or branched chain having up to 7 carbon atoms in the main chain, which is unsubstituted or substituted with one or more hydroxyl radicals and containing one or more nitrogen atoms, the nitrogen atom being substituted with an alkyl chain which is optionally interrupted by an oxygen atom and necessarily containing one or more carboxyl functions or one or more hydroxyl functions and betainized by reaction with chloroacetic acid or sodium chloroacetate.

(9) (C1-05)alkyl vinyl ether/maleic anhydride copolymers, the maleic anhydride being partially modified by semiamidation with an N,N-dialkylaminoalkylamine such as N,N-dimethyl-aminopropylamine or by semiesterification with an N,N-dialkanolamine. These copolymers can also contain other vinyl comonomers such as vinylcaprolactam.

The amphoteric film-forming polymers which are particularly preferred according to the invention are those of family (3), such as the copolymers whose CTFA name is octylacrylamide/acrylates/butylaminoethyl methacrylate copolymer, such as the products sold under the names Amphomer® LV 71 by the company Akzo Nobel.

The at least one amphoteric film forming polymer is present in the composition of the present disclosure in an amount of from about 0.05 to about 5% by weight, such as from about 0.1 to about 4% by weight, and from about 0.5 to about 3% by weight, including all ranges and subranges there-between, based on the total weight of the composition.

Neutralizer

The compositions of the present disclosure also contain a neutralizer, which affects the pH of the composition so as to allow the silicone-organic polymer hybrid compound and/or the above described film forming polymers to remain solubilized. Representative examples of neutralizers useful for this purpose include AMP (aminomethyl propanol), AMPD (aminomethyl propanediol), TIPA (triisopropanol amine), Sodium/Potassium hydroxides, Dimethylsterarylamine, Dimethyl/tallowamine lysine, ornithine, arginine, glutamic and aspartic acid. The amount of neutralizer is selected on criteria that include the desired pH of the composition. Thus, the amount of neutralizer generally ranges from greater than 0 (e.g., about 0.01%) to about 3%, and in some embodiments from 0.05% to about 2%, by weight, based on the total weight of the composition.

Cosmetically Acceptable Carrier

The cosmetically acceptable carrier of the present disclosure comprises a solvent such as water or at least one cosmetically acceptable solvent chosen from organic solvents.

The cosmetically acceptable carrier of the present disclosure may also comprise mixtures of water and at least one cosmetically acceptable solvent chosen from organic solvents.

Suitable organic solvents may be chosen from non-volatile and nonvolatile organic solvents.

Suitable organic solvents are typically C1-C4 lower alcohols, polyols alcohols and polyol ethers. Examples of organic solvents include, but are not limited to, ethanol, isopropyl alcohol, benzyl alcohol and phenyl ethyl alcohol; glycols and glycol ethers, such as propylene glycol, hexylene glycol, ethylene glycol monomethyl, monoethyl or monobutyl ether, propylene glycol and its ethers, such as propylene glycol monomethyl ether, butylene glycol, dipropylene glycol, and also diethylene glycol alkyl ethers, such as diethylene glycol monoethyl ether and monobutyl ether; hydrocarbons such as straight chain hydrocarbons, mineral oil, isododecane, polybutene, hydrogenated polyisobutene, hydrogenated polydecene, polydecene, squalene, petrolatum and isoparaffins; and mixtures, thereof.

In certain embodiments, the cosmetically acceptable carrier of the present disclosure comprises volatile organic solvents/compounds.

Preferred examples of volatile organic solvents/compounds include C2 to C4 mono-alcohols, such as ethanol, polyols such as C2-C6 glycols e.g., propylene glycol, glycerol, and polyol ethers, acetone, propylene carbonate and benzyl alcohol.

The amount of the volatile organic solvent/compound can range from greater than 0 (e.g., about 0.01%) to about 55%, or from about 0.1% to about 20%, and in some embodiments from greater than 0 to about 10%, by weight, or from about 0.01% to about 6%, by weight, or from about 0.1% to about 3.5%, by weight, based on the total weight of the composition.

In certain embodiments, it is preferred that the amount of volatile organic solvent/compound does not exceed 55%.

In some embodiments, the cosmetically acceptable carrier in the compositions of the present disclosure contains water in the amount of about 95%, 90%, 80%, 70%, 60%, 50%, 40%, 30%, 20%, 10%, 5% by weight or less, based on the total weight of the compositions. Additionally, the cosmetically acceptable carrier in the compositions of the present disclosure can contain water in the amount of from about 20% to about 95% by weight, or from about 50% to about 90% by weight, or from about 60% to about 80% by weight, based on the total weight of the compositions.

In other embodiments, the cosmetically acceptable carrier of the present disclosure comprises at least one cosmetically acceptable solvent chosen from organic solvents.

In yet some other embodiments, the cosmetically acceptable carrier of the present disclosure is substantially free of water.

Thus, the composition of the present disclosure can also be in the form of an anhydrous composition wherein the composition is substantially free of water. The term "substantially free of water" as it is used herein means that while it is preferred that no water be present in the composition, it is possible to have very small amounts of water in the compositions of the invention provided that these amounts do not materially affect at least one, preferably most, of the advantageous properties of the compositions of the invention. In particular, "substantially free of water" means that water can be present in the composition in an amount of less than about 2% by weight, or less than about 1% by weight, or less than about 0.5% by weight, or less than about 0.05% by weight of the total weight of the composition of water.

The term "water" as used in the term "substantially free of water" herein refers to water that is included as a separate ingredient in the compositions of the present disclosure and does not refer to water that may accompany one or more ingredients of a raw material that is added into the composition.

The compositions described above are useful for application onto keratinous substrates such as hair and skin.

Thus, the compositions of the present disclosure can be made into various cosmetic products such hair care products, skin care products and make up products.

Representative types of hair care compositions, including hair cosmetic and styling compositions, of the present invention include compositions for shaping the hair, maintaining the shape of the hair, styling products (e.g., gels, creams, milks, pastes, waxes, ointments, serums, foams, hair lotions, mousses, pump-sprays, non-aerosol sprays and aerosol sprays), pre-treatments and post-treatments for color protection, conditioning or protection from heat damage, leave-in hair treatments, rinse-off hair treatments, combination shampoo/styling compositions and hair volumizing compositions.

The compositions of the present disclosure can be in the form of an aqueous composition or an emulsion, such as a lotion or cream.

In one embodiment, the composition of the present disclosure is in the form of a non-aerosol spray, preferably containing a volatile organic solvent/compound.

In another embodiment, the composition of the present disclosure is in the form of a wax or a paste.

In yet another embodiment, the composition of the present disclosure is in the form of an aerosol spray, comprising a propellant.

Representative examples of propellants include C 3 to C 5 alkanes such as n-butane, isobutane, and propane, dimethyl ether (available commercially from Harp Int'l under the tradename HARP DME), C2-05 halogenated hydrocarbons, e.g., 1,1-difluoroethane (available commercially from DuPont under the tradename DYMEL 152a), difluoroethane, chlorodifluoroethane, chlorodifluoromethane, air, nitrogen, carbon dioxide, and mixtures thereof. The amount of the propellant can range from about 3 to about 90%, and in some embodiments from about 3 to about 60%, by weight, or such as from about 3 to about 20% by weight, or such as from about 3 to about 10% by weight, or such as from about 3 to about 6%, by weight based on the total weight of the composition.

Accordingly, the compositions of the present disclosure may contain at least one auxiliary ingredient, which as those skilled in the cosmetics art will appreciate, is chosen based on several criteria, including for example, the type of product and its intended use and effect, compatibility with the other ingredients, and aesthetic appeal. Representative types of such additional ingredients include rheology modifiers (also known as gelling agents or thickeners), nonionic surfactants, lipophilic compounds such as oils and waxes, and hair and skin active ingredients. Examples of these ingredients are described herein.

Rheology Modifiers

Broadly, the rheology modifier(s) that may be useful in the practice of the present invention include those conventionally used in cosmetics such as polymers of natural origin and synthetic polymers.

Representative rheology-modifying agents that may be used in the practice of the present invention include non-ionic, anionic, cationic, and amphoteric polymers, and other rheology modifiers such as cellulose-based thickeners (e.g., hydroxyethylcellulose, hydroxypropylcellulose, carboxymethylcellulose, cationic cellulose ether derivatives, quaternized cellulose derivatives, etc.), guar gum and its derivatives (e.g., hydroxypropyl guar, cationic guar derivatives, etc.), gums such as gums of microbial origin (e.g., xanthan gum, scleroglucan gum, etc.), and gums derived from plant exudates (e.g., gum arabic, ghatti gum, karaya gum, gum tragacanth, carrageenan gum, agar gum and carob gum), pectins, alginates, and starches, crosslinked homopolymers of acrylic acid or of acrylamidopropane-sulfonic acid, associative polymers, non-associative thickening polymers, and water-soluble thickening polymers.

In some embodiments, the rheology-modifying agent includes a polymer chosen from nonionic, anionic, cationic and amphoteric amphiphilic polymers.

The rheology-modifying agents may also be chosen from associative celluloses include quaternized cationic celluloses and quaternized cationic hydroxyethylcelluloses modified by groups containing at least one hydrophobic chain, such as alkyl, arylalkyl or alkylaryl groups containing at least 8 carbon atoms, and mixtures thereof.

The alkyl radicals carried by the above quaternized celluloses or hydroxyethylcelluloses may, in various embodiments, comprise from 8 to 30 carbon atoms. The aryl radicals may, for example, denote the phenyl, benzyl, naphthyl or anthryl groups. Representative examples of quaternized alkylhydroxy-ethylcelluloses containing a C8-C30 hydrophobic chain include the products Quatrisoft LM 200®, Quatrisoft LM-X 529-18-A®, Quatrisoft LM-X 529-18B® (C12 alkyl) and Quatrisoft LM-X 529-8® (Ci8 alkyl) sold by Amerchol and the products Crodacel QM®, Crodacel QL® (C12 alkyl) and Crodacel QS® (Ci8 alkyl) sold by Croda.

Representative examples of nonionic cellulose derivatives include hydroxyethylcelluloses modified by groups comprising at least one hydrophobic chain, such as alkyl, arylalkyl or alkylaryl groups, or their blends, and in which the alkyl groups are, for example, C8-C22 alkyl groups, such as the product Natrosol Plus Grade 330 CS® (C16 alkyls) sold by Aqualon or the product Bermocoll EHM 100® sold by Berol Nobel.

Representative examples of cellulose derivatives modified by alkylphenyl polyalkylene glycol ether groups include the product Amercell Polymer HM-1500® sold by Amerchol.

The rheology-modifying agent is typically present in an amount ranging from about 0.01% to about 10% by weight, in some embodiments from about 0.1% to about 5% by weight, based on the total weight of the composition.

The compositions of the present disclosure may further comprise compounds such as gellifying and viscosity modifying agents which may aid in improving the viscosity of the compositions.

Nonionic Surfactants

The compositions of the present disclosure can further comprise at least one nonionic surfactant.

Non-limiting examples of nonionic surfactants includes alkoxylated derivatives of the following: fatty alcohols, alkyl phenols, fatty acids, fatty acid esters and fatty acid amides, wherein the alkyl chain is in the C12-50 range, typically in the C16-40 range, more typically in the C24 to C40 range, and having from about 1 to about 110 alkoxy groups. The alkoxy groups are selected from the group consisting of C2-C6 oxides and their mixtures, with ethylene oxide, propylene oxide, and their mixtures being the typical alkoxides. The alkyl chain may be linear, branched, saturated, or unsaturated. Of these alkoxylated non-ionic surfactants, the alkoxylated alcohols are typical, and the ethoxylated alcohols and propoxylated alcohols are more typical. The alkoxylated alcohols may be used alone or in mixtures with those alkoxylated materials disclosed hereinabove.

Commercially available nonionic surfactants are Brij® nonionic surfactants from Croda, Inc., Edison, N.J. Typically, Brij® is the condensation products of aliphatic alcohols with from about 1 to about 54 moles of ethylene oxide, the alkyl chain of the alcohol being typically a linear chain and having from about 8 to about 22 carbon atoms, for example, Brij® 72 (i.e., Steareth-2) and Brij® 76 (i.e., Steareth-10).

Also useful herein as nonionic surfactants are alkyl glycosides, which are the condensation products of long chain alcohols, which are the condensation products of long chain alcohols, e.g. C8-C30 alcohols, with sugar or starch polymers. These compounds can be represented by the formula (S)n-O—R wherein S is a sugar moiety such as glucose, fructose, mannose, galactose, and the like; n is an integer of from about 1 to about 1000, and R is a C8-C30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants are alkyl polyglucosides wherein S is a glucose moiety, R is a C8-C20 alkyl group, and n is an integer of from about 1 to about 9. Commercially available examples of these surfactants include decyl polyglucoside (available as APG® 325 CS) and lauryl polyglucoside (available as APG® 600CS and 625 CS), all the above-identified polyglucosides APG® are available from Cognis, Ambler, Pa. Also useful herein sucrose ester surfactants such as sucrose cocoate and sucrose laurate.

Other nonionic surfactants suitable for use in the present invention are glyceryl esters and polyglyceryl esters, including but not limited to, glyceryl monoesters, typically glyceryl monoesters of C16-C22 saturated, unsaturated and branched chain fatty acids such as glyceryl oleate, glyceryl monostearate, glyceryl monoisostearate, glyceryl monopalmitate, glyceryl monobehenate, and mixtures thereof, and polyglyceryl esters of C16-C22 saturated, unsaturated and branched chain fatty acids, such as polyglyceryl-4 isostearate, polyglyceryl-oleate, polyglyceryl-2 sesquioleate, triglyceryl diisostearate, diglyceryl monooleate, tetraglyceryl monooleate, and mixtures thereof.

Also useful herein as nonionic surfactants are sorbitan esters. Preferable are sorbitan esters of C16-C22 saturated, unsaturated and branched chain fatty acids. Because of the manner in which they are typically manufactured, these sorbitan esters usually comprise mixtures of mono-, di-, tri-, etc. esters. Representative examples of suitable sorbitan esters include sorbitan monooleate (e.g., SPAN® 80), sorbitan sesquioleate (e.g., Arlacel® 83 from Croda, Inc., Edison, N.J.), sorbitan monoisostearate (e.g., CRILL® 6 from Croda, Inc., Edison, N.J.), sorbitan stearates (e.g., SPAN® 60), sorbitan trioleate (e.g., SPAN® 85), sorbitan tristearate (e.g., SPAN® 65), sorbitan dipalmitates (e.g., SPAN® 40), and sorbitan isostearate. Sorbitan monoisostearate and sorbitan sesquioleate are particularly preferred emulsifiers for use in the present invention.

Also suitable for use as nonionic surfactants are alkoxylated derivatives of glyceryl esters, sorbitan esters, and alkyl polyglycosides, wherein the alkoxy groups are selected from the group consisting of C2-C6 oxides and their mixtures, with ethoxylated or propoxylated derivatives of these materials being typical. Nonlimiting examples of commercially available ethoxylated materials include TWEEN® (ethoxylated sorbitan mono-, di- and/or tri-esters of C12 to C18 fatty acids with an average degree of ethoxylation of from about 2 to 20).

One type of preferred nonionic surfactants include alkoxylated alcohols such as a polyethylene derivative of hydrogenated castor oil, for example, PEG-40 hydrogenated castor oil, commercially available from the company Cognis (BASF) under the tradename Eumulgin® HRE 40 or Cremophor® CO 40.

The at least one nonionic surfactant is typically present in an amount from about 0.5 by weight to about 30% by weight, typically in an amount from about 1 by weight to about 20% by weight and more typically from about 0.5 by weight to 10% by weight, including all ranges and subranges there-between, based on the total weight of the composition of the present disclosure.

Lipophilic Compounds

The compositions of the present disclosure can further comprise at least one lipophilic compound which can be chosen from oils, fatty esters, hydrocarbon oils, waxes, fatty acids and salts thereof, fatty alcohols, lipophilic vitamins and esters thereof, organic sunscreens, phospholipids, and mixtures thereof.

Oils that may be suitable for use in the present invention include both volatile and nonvolatile oils. The volatile or nonvolatile oils are typically selected from hydrocarbon-based oils, silicone oils, and fluoro oils. The term "hydrocarbon-based oil" refers to oil mainly containing hydrogen and carbon atoms and possibly oxygen, nitrogen, sulfur and/or phosphorus atoms.

Non-limiting examples of oils include plant oils such as olive oil, avocado oil, coconut oil, safflower oil, almond oil, castor oil, jojoba oil, peanut oil, sesame oil, hazelnut oil, sunflower oil, apricot kernel oil, grapeseed oil, palm oil, argan oil, squalane and pracaxi oil.

Non-limiting examples of synthetic oils and hydrocarbon oils include mineral oil, petrolatum, and $C_{10}$-$C_{40}$ hydrocarbons which may be aliphatic (with a straight, branched or cyclic chain), aromatic, arylaliphatic such as paraffins, isoparaffins, isododecanes, aromatic hydrocarbons, and mixtures thereof.

Non-limiting examples of waxes include paraffin wax, beeswax, candelilla wax, carnauba wax, jasmine wax, jojoba wax and mimosa wax.

Suitable fatty acids include those containing from 8 to 30, preferably from 12 to 24 carbon atoms, and carboxylate salts of fatty acids. The sodium, potassium, ammonium, calcium and magnesium carboxylates of fatty acids listed are typical examples of the carboxylate salts of the fatty acids.

Non-limiting preferred examples of fatty alcohols include compounds of formula:

where R represents a hydrocarbon radical containing at least three carbon atoms, preferably from 8 to 30, more preferably from 12 to 24 carbon atoms, and which may be linear or branched, acyclic or cyclic, saturated or unsaturated, aliphatic or aromatic, substituted or unsubstituted.

Typically, R is a linear or branched, acyclic alkyl or alkenyl group or an alkyl phenyl group.

Non-limiting preferred fatty esters include esters formed from fatty acids and $C_{1-10}$ alcohols and esters formed from the fatty alcohols as defined hereabove and $C_{1-10}$ carboxylic acids.

In addition, non-limiting specific examples of lipophilic compounds include isopropyl palmitate, capric/caprylic triglyceride, isodecyl neopentanoate, polyIsobutylene, Phloretin, Ellagic acid, Vitamin D, Vitamin E, Vitamin E Acetate, Vitamin A, Vitamin A Palmitate, 2-oleamido-1,3-octadecanediol, octyl methoxycinnamate, octyl salicylate, 18-Methyleicosanoic acid, and mixtures thereof. Other types of lipophiles include organic sunscreens, phospholipids, other water-insoluble vitamins, and other natural and synthetic oils.

Representative examples of volatile hydrocarbon-based oils include oils containing from 8 to 16 carbon atoms, and especially branched C8-C16 alkanes (also known as isoparaffins), for instance isododecane (also known as 2,2,4,4,6-pentamethylheptane), isodecane and isohexadecane.

Examples of nonvolatile silicone oils that may be useful in the present invention include nonvolatile polydimethylsiloxanes (PDMS), polydimethylsiloxanes comprising alkyl or alkoxy groups that are pendent and/or at the end of a silicone chain, these groups each containing from 2 to 24 carbon atoms, phenyl silicones, for instance phenyl trimethicones, phenyl dimethicones, phenyl trimethylsiloxy diphenylsiloxanes, diphenyl dimethicones, diphenyl methyldiphenyl trisiloxanes and 2-phenylethyl trimethylsiloxysilicates, and dimethicones or phenyltrimethicones with a viscosity of less than or equal to 100 cSt.

Representative examples of volatile silicone oils that may be useful in the present invention include volatile linear or cyclic silicone oils, especially those with a viscosity ÿ centistokes (8×10-6 m 2/s) and especially containing from 2 to 10 silicon atoms and in particular from 2 to 7 silicon atoms, these silicones optionally comprising alkyl or alkoxy groups containing from 1 to 10 carbon atoms. Specific examples include dimethicones with a viscosity of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Representative examples of volatile fluoro oils that may be suitable for use in the present invention include nonafluoromethoxybutane and perfluoro-methylcyclopentane.

According to one embodiment, the at least one lipophilic compound is chosen from plant oils, hydrocarbon oils, synthetic oils, fatty acids having at least 12 carbon atoms, fatty esters and mixtures thereof.

According to another embodiment, the at least one lipophilic compound comprises fragrance oils.

The at least one lipophilic compound is present in the composition of the present disclosure in an amount of from about 0.1 to about 20% by weight, such as from about 0.3 to about 10% by weight, and from about 0.5 to about 5% by weight, including all ranges and subranges there-between, based on the total weight of the composition.

As skin and hair active agents that may be used in the composition of the present disclosure, examples that may be mentioned include moisturizers, for example, protein hydrolysates and polyols such as glycerol, glycols, for instance polyethylene glycols, and sugar derivatives; natural and plant extracts; anti-inflammatory agents; antioxidants; anti-wrinkle agents; procyannidol oligomers; vitamins, for instancevitamin A (retinol), vitamin C (ascorbic acid), vitamin E (tocopherol), vitamin B5 (panthenol), vitamin B3 (niacinamide), derivatives of these vitamins (especially esters) and mixtures thereof; urea; caffeine; depigmenting agents such as kojic acid, hydroquinone and caffeic acid; salicylic acid and its derivatives; α-hydroxy acids such as lactic acid and glycolic acid and derivatives thereof; β-hydroxy acids, α-keto acids, β-keto acids, retinoids such as carotenoids and vitamin A derivatives; sunscreens; self-tanning agents; hydrocortisone; melatonin; algal, fungal, plant, yeast or bacterial extracts; enzymes; DHEA and its derivatives and metabolites; antibacterial active agents, for instance 2,4,4'-trichloro-2'-hydroxydi-phenyl ether (or Triclosan), 3,4,4'-trichloro-carbanilide (or Triclocarban); mattifying agents and mixtures thereof.

Non-limiting examples of sunscreens include benzophenones, bornelone, butyl PABA, cinnamidopropyl trimethyl ammonium chloride, disodium distryrylbiphenyl disulfonate, PABA, potassium methoxycinnamate, butyl methoxydibenzoylmethane, octyl methoxycinnamate, oxybenzone, octocrylene, octyl salicylate, phenylbenzimidazole sulfonic acid, ethyl hydroxypropyl aminobenzoate, menthyl anthranilate, aminobenzoic acid, cinoxate, diethanolamine methoxycinnamate, glyceryl aminobenzoate, titanium dioxide, zinc oxide, oxybenzone, ethylhexyl dimethyl PABA, red petrolatum, and mixtures thereof.

Non-limiting examples of preservatives include polyvinyl alcohol, phenoxyethanol, benzyl alcohol, methyl paraben, propyl paraben and mixtures thereof.

Non-limiting examples of pH adjusting agents include potassium acetate, sodium carbonate, sodium hydroxide, phosphoric acid, succinic acid, sodium citrate, citric acid, boric acid, lactic acid, sodium hydrogen carbonate and mixtures thereof.

Yet other examples of auxiliary ingredients that may be present in the inventive compositions include fragrances, preservatives, colorants, glitter, fillers/powders, buffers, chelators (such as EDTA and salts thereof, particularly sodium and potassium salts), reducing agents, plasticizers, softeners, antifoaming agents, inorganic colloids, peptizing agents, pearlescent agents, penetrants, opacifying agents, silicones, and any other additive or adjuvant conventionally used in cosmetic compositions intended to be applied to the hair. The compositions may further contain polymers other than the silicone-organic polymer hybrid compound of the invention, provided that they are compatible with the other ingredients therein.

The at least one auxiliary ingredient is present in the composition in a preferred amount of from about 0.001 to about 50% and more preferably from about 0.01 to about 20% by weight, based on the total weight of the composition.

One embodiment of the present disclosure is a cosmetic composition comprising, in a cosmetically acceptable carrier, at least one silicone-organic polymer hybrid compound, at least one nonionic film forming polymer, at least one amphoteric film forming polymer, and at least one neutralizer.

In one embodiment, the composition of the present disclosure is a composition for shaping the hair and/or maintaining the shape of hair, such as a styling composition.

In other embodiments, the composition of the present disclosure additionally contains a volatile organic solvent/compound.

In one preferred embodiment the composition of the present disclosure is in the form of a spray composition.

In other embodiments the composition of the present disclosure contains a propellant.

In yet other embodiments the composition of the present disclosure does not contain a propellant.

In one embodiment, the composition of the present disclosure does not contain an anionic polymer other than the silicone-organic polymer hybrid compound of the present disclosure.

In other embodiments, the composition of the present disclosure is a composition for the care of skin and/or hair.

Method of Use

The method or process of using the compositions of the present disclosure will depend on the keratinous substrate being targeted and, consequently, the specific ingredients contained in the composition used to effectuate the treatment. One of ordinary skill in the art will easily be able to determine these variables.

An embodiment of the present invention is a method of caring for a keratinous substrate such as skin or hair.

A preferred embodiment of the present invention is a method of imparting shape to or maintaining the shape of hair comprising applying onto the hair, the above-described composition.

According to at least one embodiment, such a method comprises applying to the hair, an effective amount of the composition.

An effective amount of the composition, typically from about 0.1 gram to about 50 grams, preferably from about 0.5 gram to about 20 grams of the composition. Application to the hair typically includes working the composition through the hair.

The compositions may be applied to wet or dry hair, before or after shaping. They may be used in a non-rinse fashion in order to impart or maintain the shape of the hair. In some other embodiments, the composition may be rinsed from the hair. In some embodiments, following application of the composition, the hair is dried (e.g., air or blow dried), or dried in conjunction with the use of shaping tools and/or heating tools such as a hot iron, e.g., flat iron or curling iron, blow dryer, and hood dryer. Other shaping tools may be chosen from combs and brushes.

Embodiments of the present invention will now be described in terms of the following non-limiting working examples. Unless indicated to the contrary, all parts are by weight.

The following examples are for illustrative purposes only and are not intended to limit the scope of the claims.

EXAMPLES

Example 1

Formulation Examples, Table 1

| INCI US | Formula A Inventive formula | Formula B Comparative formula |
|---|---|---|
| CROTONIC ACID/VINYL C8-12 ISOALKYL ESTERS/VA/BIS-VINYLDIMETHICONE CROSSPOLYMER | 2.5 | 2.5 |
| VP/VA COPOLYMER | 1.75 | — |
| OCTYLACRYLAMIDE/ACRYLATES/BUTYLAMINOETHYL METHACRYLATE COPOLYMER | 2.18 | — |

-continued

| INCI US | Formula A Inventive formula | Formula B Comparative formula |
|---|---|---|
| AMINOMETHYL PROPANOL | 0.62 | 0.62 |
| PEG-40 HYDROGENATED CASTOR OIL | 1.5 | 1.5 |
| FRAGRANCE, TOCOPHEROL, PRESERVATIVES | 0.80 | 0.80 |
| XYLOSE | 0.1 | 0.1 |
| ALCOHOL DENAT. | 6.00 | 6.00 |
| WATER | QS 100 | QS 100 |

Procedure of Making:

1. In side phase A, water was added to a suitably sized vessel.
2. Aminomethyl Propanol, Octylacrylamide/acrylates/butylaminoethyl methacrylate copolymer, and VP/VA Copolymer were added and mixed into the water to form a uniform mixture.
3. Xylose was added and mixed into the mixture.
4. Preservatives were added and mixed into the mixture.
5. In side phase B, PEG-40 Hydrogenated Castor Oil was melted to 45-50° C. Fragrance was added and mixed until uniformity. Phase B was added to phase A.
6. Alcohol was added to the mixture of phases A and B and mixed until uniformity.
7. In side phase C, Crotonic Acid/Vinyl C8-12 Isoalkyl Esters/VA/Bis-vinyldimethicone crosspolymer was combined with Aminomethyl Propanol and mixed until uniform. Side phase C was added to the combined phases A and B.

The preparation of Formula B did not require step 2 in the procedure above.

The formula examples above were formulated as spray compositions which were applied onto hair swatches according to the following procedure of cosmetically treating/coating and shaping the hair:

One-inch thick hair swatches were prepared from European hair (commercially available), naturally wavy hair.

Five sprays of each formula to be tested were applied to a designated swatch resulting in coated swatches; five sprays amounted to about 0.6 grams of a test formula.

Each coated swatch was combed through three times.

Each swatch was then subjected to up to seven passes of a flat iron set to 410° F.

Each swatch was then combed through three times.

Following the procedure above, although all the test swatches had a smooth feel and noticeable shine, the swatches coated with the inventive formula (A) were noticeably more texturized (gave a feeling of more hold and form to the hair upon touching the hair) and their shapes were better maintained (better styling hold). In addition, it took only three passes of the flat iron to effectively smooth out the hair coated with formula A whereas it took seven passes of the flat iron to effectively smooth out the hair coated with the comparative formula (B). Thus, the use of the inventive formula resulted in a more time efficient process of styling/shaping the hair. In addition, the presence of the additional film forming polymers, Octylacrylamide/acrylates/butylaminoethyl methacrylate copolymer, and VP/VA Copolymer, did not weigh the hair down nor adversely affect the performance of the silicone-organic polymer hybrid compound.

Example 2

Inventive Formulas without Alcohol

The formula A in example 1 was also formulated as a paste and as a wax (containing additional wax ingredients) without adding alcohol as a separate ingredient.

The inventive wax formula was applied onto the hair of one half side of a mannequin head and a comparative formula which did not contain the Crotonic Acid/Vinyl C8-12 Isoalkyl Esters/VA/Bis-vinyldimethicone crosspolymer was applied to the hair of the other half side of the mannequin head.

The inventive paste formula was similarly applied onto the hair of one half side of a mannequin head and a comparative formula which did not contain the Crotonic Acid/Vinyl C8-12 Isoalkyl Esters/VA/Bis-vinyldimethicone crosspolymer was applied to the hair of the other half side of the mannequin head.

The hair treated with the inventive wax and paste formulas resulted in a more finished look to the hair, disciplined ends of the hair (more hold and control), smoother feel, and more shine.

Example 3

Comparative Examples, Table 2

| INCI name/ingredients | Formula C % wt | Formula D % wt | Formula E % wt | Formula F (inventive composition) % wt |
| --- | --- | --- | --- | --- |
| CROTONIC ACID/VINYL C8-12 ISOALKYL ESTERS/VA/BIS-VINYLDIMETHICONE CROSSPOLYMER | 2.5 | 2.5 | 2.5 | 2.5 |
| ALCOHOL DENAT. | 3.5 | 3.5 | 3.5 | 3.5 |
| OCTYLACRYLAMIDE/ACRYLATES/BUTYLAMINOETHYL METHACRYLATE COPOLYMER | — | 2.43 | — | 1.21 |
| VP/VA COPOLYMER | — | — | 2.5 | 1.25 |
| AMINOMETHYL PROPANOL (for neutralization of the silicone-organic polymer hybrid compound) | 0.13 | 0.66 | 0.01 | 0.4 |
| WATER | QS 100 | QS 100 | QS 100 | QS 100 |

Formulas C to F in Table 2 were made according to the procedure of making in example 1 above.

The formula examples above were formulated as spray compositions which were applied onto hair swatches according to the following procedure of cosmetically treating/coating and shaping the hair:

One half centimeter-inch thick and 8 inch long hair swatches were prepared.

Three sprays of each formula to be tested were applied to designated swatches resulting in coated swatches; three sprays amounted to about 0.43±0.03 grams of a test formula.

Each coated swatch was combed through three times.

Each swatch was then curled using a Conair Instant Heat curling iron at a setting of 17, holding the hair curled along the curling iron for six seconds per curling step.

Following the procedure above, the swatch coated with the inventive composition, formula F, exhibited the most discipline and compact curl, that is, no frayed ends, no static-induced individualized hair fibers, compared to those coated with the other test formulas. Moreover, the swatch coated with formula F was just as smooth and silky as the swatch coated with formula C (which did not contain the film forming polymers) and more smooth and silky than the swatch coated with formula D which indicates that the presence of the amphoteric and nonionic film forming polymers did not make the hair undesirably stiff nor did their presence result in a brittle or hard film on the hair. Thus, these film forming polymers did not negatively impact the performance of the silicone-organic polymer hybrid compound but instead, significantly contributed to the efficacious performance of the inventive composition. Overall, the combination of polymers in the inventive composition boosted the hold level of each of the polymers and provided compactness and discipline to the curled hair, without sacrificing the suppleness and bounce of the curl and the smooth feel attributed to the silicone-organic polymer hybrid compound.

The foregoing description illustrates and describes the present disclosure. Additionally, the disclosure shows and describes only the preferred embodiments of the disclosure, but, as mentioned above, it is to be understood that it is capable of changes or modifications within the scope of the concept as expressed herein, commensurate with the above teachings and/or skill or knowledge of the relevant art. The embodiments described hereinabove are further intended to explain best modes known of practicing the invention and to enable others skilled in the art to utilize the disclosure in such, or other, embodiments and with the various modification required by the particular applications or uses disclosed herein. Accordingly, the description is not intended to limit the invention to the form disclosed herein. Also, it is intended that the appended claims be construed to include alternative embodiments.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

What is claimed is:

1. A composition comprising, in a cosmetically acceptable carrier:
    (a) at least one silicone-organic polymer hybrid compound;
    (b) at least one nonionic film forming polymer present in an amount of from about 0.5% to about 5% by weight;

(c) at least one amphoteric film forming polymer present in an amount of from about 0.5% to about 3% by weight;

(d) at least one neutralizer; and wherein the cosmetically acceptable carrier comprises a combination of water and at least one organic solvent chosen from volatile organic solvents wherein the at least one organic solvent is present in an amount of from about 0.01 to about 10% by weight; wherein all weights are based on the total weight of the composition; and wherein (a) is Crotonic Acid/Vinyl C8-12 Isoalkyl Esters/VA/Bis-Vinyldimethicone Crosspolymer; (b) is chosen from vinyl pyrrolidone/vinyl acetate copolymer, polyvinylpyrrolidone and mixtures thereof; and (c) is octylacrylamide/acrylates/butylaminoethyl methacrylate copolymer.

2. The composition of claim 1, wherein (a) is present in an amount of from about 0.05 to about 20% by weight, based on the total weight of the composition.

3. The composition of claim 1, wherein (b) is vinyl pyrrolidone/vinyl acetate copolymer.

4. The composition of claim 1, further comprising at least one auxiliary ingredient selected from the group consisting of propellants, rheology modifiers, emulsifiers, surfactants, fatty phase ingredients, preservatives and fragrances, and combinations of two or more thereof.

5. The composition of claim 1, further comprising a propellant.

6. The composition of claim 1, wherein the composition is in the form of a spray.

7. The composition of claim 1, wherein the composition does not contain a propellant.

8. The composition of claim 1, wherein the composition is a composition for imparting shape to hair or maintaining shape of hair.

9. The composition of claim 1, wherein the cosmetically acceptable carrier comprises water and a volatile organic solvent and wherein the volatile organic solvent is present in an amount of from about 0.01 to about 6%, based on the total weight of the composition.

10. A composition for imparting shape to hair or maintaining shape of hair comprising, in a cosmetically acceptable carrier:

(a) from about 1% to about 3% by weight of Crotonic Acid/Vinyl C8-12 Isoalkyl Esters/VA/Bis-Vinyldimethicone Crosspolymer;

(b) from about 0.5% to about 5% by weight of at least one nonionic film forming polymer;

(c) from about 0.5% to about 3% by weight of at least one amphoteric film forming polymer;

(d) at least one neutralizer;

all weights being based on the total weight of the composition; wherein the cosmetically acceptable carrier comprises a combination of water and at least one organic solvent chosen from volatile organic solvents wherein the at least one organic solvent is present in an amount of from about 0.01 to about 10% by weight; and wherein (b) is chosen from vinyl pyrrolidone/vinyl acetate copolymer, polyvinylpyrrolidone and mixtures thereof; and (c) is octylacrylamide/acrylates/butylaminoethyl methacrylate copolymer.

11. The composition of claim 10, wherein the cosmetically acceptable carrier comprises water and a volatile organic solvent and wherein the volatile organic solvent is present in an amount of from about 0.01 to about 6%, based on the total weight of the composition.

12. A method of imparting shape to hair or maintaining shape of hair, comprising applying to hair, a composition, containing, in a cosmetically acceptable carrier:

(a) at least one silicone-organic polymer hybrid compound;

(b) at least one nonionic film forming polymer present in an amount of from about 0.5% to about 5% by weight;

(c) at least one amphoteric film forming polymer present in an amount of from about 0.5% to about 3% by weight;

(d) at least one neutralizer; and wherein the cosmetically acceptable carrier comprises a combination of water and at least one organic solvent chosen from volatile organic solvents wherein the at least one organic solvent is present in an amount of from about 0.01 to about 10% by weight; wherein all weights are based on the total weight of the composition; and wherein (a) is Crotonic Acid/Vinyl C8-12 Isoalkyl Esters/VA/Bis-Vinyldimethicone Crosspolymer; (b) is chosen from vinyl pyrrolidone/vinyl acetate copolymer, polyvinylpyrrolidone and mixtures thereof; and (c) is octylacrylamide/acrylates/butylaminoethyl methacrylate copolymer.

13. The method of claim 12, further comprising applying heat to the hair after applying the composition onto the hair.

14. The method of claim 12, further comprising applying a device chosen from a flat iron, a curling iron, a comb and a brush to the hair after applying the composition onto the hair.

15. The method of claim 12, wherein the cosmetically acceptable carrier comprises water and a volatile organic solvent and wherein the volatile organic solvent is present in an amount of from about 0.01 to about 6%, based on the total weight of the composition.

* * * * *